United States Patent [19]

Fain et al.

[11] Patent Number: 5,075,323
[45] Date of Patent: Dec. 24, 1991

[54] COMPOUNDS INCLUDING OMEPRAZOLE IN THE TREATMENT OF GLAUCOMA

[75] Inventors: Gordon L. Fain; David A. Lee, both of Los Angeles, Calif.; Per L. Lindberg, Askim, Sweden; George Sachs, Cure Wadsworth, Calif.

[73] Assignee: Aktiebolaget Hassle, Molndal, Sweden

[21] Appl. No.: 399,429

[22] Filed: Aug. 23, 1989

Related U.S. Application Data

[63] Continuation of Ser. No. 235,996, Aug. 24, 1988, abandoned, which is a continuation-in-part of Ser. No. 235,918, Aug. 23, 1988, abandoned.

[51] Int. Cl.$^5$ ............................................. A61K 31/44
[52] U.S. Cl. ..................................................... 514/338
[58] Field of Search ......................................... 514/338

[56] References Cited

U.S. PATENT DOCUMENTS 4,359,465  11/1982  Ruwart .................................. 514/314

FOREIGN PATENT DOCUMENTS 0005129  10/1979  European Pat. Off. .

OTHER PUBLICATIONS

Drug Development Research, vol. 10, No. 4, 1987, Maren, Thomas H.: "Carbonic anhydrase: General perspectives and advances in glaucoma research", pp. 255-276.

Primary Examiner—Douglas W. Robinson
Assistant Examiner—Zohreh A. Fay
Attorney, Agent, or Firm—White & Case

[57] ABSTRACT

A method for the treatment of diseases related to an increased intraocular pressure in the eye comprising administration to a patient suffering therefrom an amount of a compound of the formula I

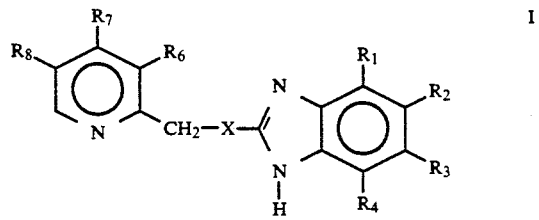

or a pharmaceutically acceptable salt thereof.

5 Claims, No Drawings

COMPOUNDS INCLUDING OMEPRAZOLE IN THE TREATMENT OF GLAUCOMA

This application is a continuation of application Ser. No. 235,996, filed Aug. 24, 1988, which is a continuation-in part of application Ser. No. 235,918 filed Aug. 23, 1988, both now abandoned.

FIELD OF THE INVENTION

The present invention relates to a novel method for the treatment of disorders of the human eye, particularly glaucoma.

BACKGROUND OF THE INVENTION

Glaucoma is characterized by increased intraocular pressure resulting at least in part, from a diminished outflow of aqueous humor through the trabecular meshwork. Glaucoma is an eye disease which untreated can lead to blindness. The disease is one of the principal reasons to blindness in Europe and U.S.A. The disease generally begins insidious without any trouble for the patient. Gradually the symptoms arise in the shape of loss of field of vision and sight degeneration which grow worse if the glaucoma is not treated. Normally the production and outflow of aqueous humor in the eye are in balance. Is this balance disturbed either by increase in aqueous humor production or, more usually, diminished outflow of aqueous humor the pressure in the eye is increased. The high intraocular pressure has an injurious effect on sight cells as well as on nervepaths in the eye and leads to progressive lesions on these structures. The pressure can be decreased by increasing the outflow of aqueous humor.

PRIOR ART

Heterocyclylalkylsulfinylbenzimidazoles and heterocyclylalkylthiobenzimidazoles are known in the art, as are methods for using these compounds to reduce gastric acid secretion.

OUTLINE OF THE PRESENT INVENTION

According to the present invention it has been found that compounds of the general formula I as well as pharmaceutically acceptable salts thereof are effective to decrease the intraocular pressure in eyes and are thus useful as medicals for the treatment of disorders of the human eye, particularly glaucoma.

The compounds of the formula I below are in most cases known. Compounds which are not known in the prior art can be prepared by methods known for analogous compounds.

The compounds of the invention are of the following formula I:

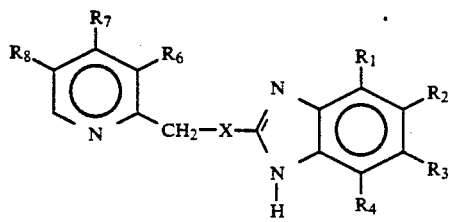

wherein
X is —S— or —S—;

$R^1$, $R^2$, $R^3$ and $R^4$, which are the same or different, are
(a) H
(b) alkyl containing 1-8, especially 1-6 carbon atoms
(c) alkoxy containing 1-8, especially 1-6 carbon atoms
(d) alkoxyalkyl containing 1-3 carbon atoms in each alkyl part
(e) alkoxyalkoxy containing 1-3 carbon atoms in each alkyl part
(f) halogen
(g) CN
(h) —$CF_3$
(i) —$NO_2$
(j) —$COR^{10}$
(k) alkylthio containing 1-6 carbon atoms in the alkyl part
(l) alkylsulfinyl containing 1-7 carbon atoms in the alkyl part
(m) aryl-thio, -sulfinyl, -sulfonyl, -sulfonyloxy, -oxysulfonyl, -sulfonamido or -aminosulfonyl, whereby each aryl group optionally is substituted by 1-3 substituents, the same or different and selected from halogen, $CP_3$ and (1-5C)alkoxy
(n) arylalkyl or arylalkoxy, containing 1-6 carbon atoms in the alkyl and alkoxy parts, respectively, whereby the aryl part optionally is substituted by 1-3 substituents, the same or different and selected from halogen, $CF_3$, (1-5C)alkyl and (1-5C)alkoxy
(o) aryl or aryloxy, whereby each aryl group optionally is substituted by 1-3 substituents, the same or different and selected from halogen, $CF_3$, (1-5C)alkyl and (1-5C)alkoxy
(p) haloalkoxy containing 1-6 carbon atoms and 1-11 halogen atoms, especially 1-6 halogen atoms
(q) hydroxyalkyl containing 1-6 carbon atoms
(r) $R^1$ and $R^2$, $R^2$ and $R^3$ or $R^3$ and $R^4$ together with the adjacent carbon atoms in the benzimidazole ring form one or more 5-, 6- or 7-membered rings, which each may be saturated or unsaturated and may contain 0-3 hetero atoms selected from N, S and O, and whereby each ring may be optionally substituted with 1-10, suitably 1-6, or 1-4 substituents selected from alkyl groups with 1-3 carbon atoms and halogen or two or four of the mentioned substituents together form one or two oxo groups (C=O), whereby if $R^1$ and $R^2$, $R^2$ and $R^3$ or $R^3$ and $R^4$ together with the adjacent carbon atoms in the benzimidazole ring form two rings the rings may be condensed with each other;

$R^6$ is
(a) H
(b) alkyl containing 1-8, especially 1-6 carbon atoms
(c) alkoxy containing 1-8, especially 1-6 carbon atoms
(d) halogen $R^8$ is
(a) H
(b) alkyl containing 1-8, especially 1-6 carbon atoms
(c) alkoxy containing 1-6 carbon atoms (d) halogen
(e) arylalkyl containing 1–4 carbon atoms in the alkyl part $R^7$ is
(a) H
(b) alkyl containing 1–7 carbon atoms
(c) alkoxy containing 1–7 carbon atoms
(d) alkoxyalkyl containing 1–3 carbon atoms in each alkyl part
(e) alkoxyalkoxy containing 1–3 carbon atoms in each alkyl part
(f) aryloxy, whereby the aryl group optionally is substituted by 1 or 2 substituents, the same or different and selected from halogen, $CF_3$, (1-3C)alkyl or (1-3C)alkoxy
(g) arylalkyl or arylalkoxy containing 1–7 carbon atoms in the alkyl resp. alkoxy part, whereby the aryl part optionally is substituted by 1 or 2 substituents, the same or different and selected from halogen, $CF_3$, (1-3C)alkyl and (1-3C)alkoxy
(h) alkenyloxy containing 1–7 carbon atoms in the alkenyl part
(i) alkynyloxy containing 1–7 carbon atoms in the alkenyl part
(j) alkylthio containing 1–7, preferably 1–3 carbon atoms in the alkyl part
(k) arylthio or arylalkylthio containing 1–3, preferably 1 carbon atom in the alkyl part
(l) dialkylamino containing 1–7, preferably 1–3 carbon atoms in the alkyl parts
(m) morpholino
(n) piperidino
(o) N-methylpiperazino
(p) pyrrolidino
(q) fluoroalkoxy containing 2–5 carbon atoms and 1–9 fluorino atoms or $R^6$ and $R^7$, or $R^7$ and $R^8$ together with the adjacent carbon atoms in the pyridine ring form a 5- or 6-membered, saturated or unsaturated ring, which may optionally contain an oxygen, sulphur or an optionally alkylated nitrogen atom;

$R^{10}$ is
(a) alkyl containing 1–6 carbon atoms
(b) alkoxy containing 1–6 carbon atoms
(c) aryl;

as well as pharmaceutically acceptable salts thereof, especially alkali salts such as sodium and potassium salts.

Illustrative examples of the various radicals in the formula I are as follows. These illustrative examples will be applicable to the different radicals depending on the number of carbon atoms prescribed for each radical.

The group alkyl in the definitions of $R^1$, $R^2$, $R^3$, $R^4$, $R^6$, $R^7$, $R^8$, $R^{10}$ are exemplified by methyl, ethyl, n-propyl, isopropyl, n-butyl, isobutyl, t-butyl, n-pentyl, n-hexyl, cyclopropyl, cyclopentyl, cyclohexyl, cyclopropylmethyl, cyclopentylmethyl, cyclopentylethyl, and cyclohexylmethyl. Lower alkyl groups containing 1–4 carbon atoms are especially preferred.

The group alkoxy in the definitions of $R^1$, $R^2$, $R^3$, $R^4$, $R^6$, $R^7$, $R^8$ and $R^{10}$ are exemplified by methoxy, ethoxy, n-propoxy, iso-propoxy, n-butoxy, i-butoxy, s-butoxy, t-butoxy, n-pentoxy, i-pentoxy, n-hexoxy, cyclopropoxy, cyclopentoxy, cyclohexoxy, cyclopropylmethoxy, cyclopentylmethoxy, cyclopentylethoxy, and cyclohexylmethoxy. Lower alkoxy groups are preferred, especially those containing 1–4 carbon atoms, preferably a lower alkoxy group having especially preferred 1–3 carbon atoms, e.g. methoxy, ethoxy, n-propoxy or isopropoxy.

Halogen in the definitions of $R^1$, $R^2$, $R^3$ and $R^4$ is chloro, bromo, fluoro and iodo, preferably chloro, bromo, and fluoro.

In $R^1$, $R^2$, $R^3$, $R^4$ and $R^7$ when representing alkylthio or alkylsulfinyl the alkyl is preferably a lower alkyl having especially preferred 1–4 carbon atoms, e.g. methylthio, methylsulfinyl, ethylthio, ethylsulfinyl, isopropylthio, n-butylsulfinyl or isobutylthio.

The group aryl when present in $R^1$, $R^2$, $R^3$, $R^4$, $R^7$, $R^{10}$ has preferably up to 10 carbon atoms, especially preferred up to 6 carbon atoms, e.g. a phenyl group.

$R^1$, $R^2$, $R^3$, $R^4$ and $R^7$ representing an aryloxy or arylthio group have preferably up to 10 carbon atoms, especially preferred up to 6 carbon atoms, e.g. a phenoxy or phenylthio group.

The groups arylalkyl, arylalkoxy, and arylalkylthio, when present in $R^1$, $R^2$, $R^3$, $R^4$, $R^5$, $R^7$, $R^8$ have preferably up to 10 carbon atoms in the aryl group. Especially preferred are 6 carbon atoms in the aryl group and 1–3 carbon atoms in the alkyl group or alkoxy group, respectively, e.g. phenylmethyl, phenylethyl, phenylmethoxy, phenylethoxy, phenylpropyl, phenylisopropoxy, phenylmethylthio, and phenylethylthio.

$R^1$, $R^2$, $R^3$, $R^4$ and $R^7$ representing an alkoxyalkyl or alkoxyalkoxy group are exemplified by methoxymethyl, methoxyethyl, methoxypropyl, ethoxymethyl, ethoxyethyl, propoxyethyl, methoxymethoxy, methoxyethoxy, methoxypropoxy, ethoxyethoxy and propoxyethoxy.

$R^7$ representing an alkenyloxy or alkynyloxy group has preferably 2–7 carbon atoms, especially preferred 3–4 carbon atoms, e.g. allyloxy, propargyloxy, 2-butenyloxy and 2-butynyloxy.

Illustrative examples of ring structures formed by $R^1$ and $R^2$, $R^2$ and $R^3$ and $R^3$ and $R^4$ are $-CH_2CH_2CH_2-$, $-CH_2CH_2CH_2CH_2-$, $-CH_2C(CH_3)_2CH_2-$, $-CH_2)_5-$, $-CH=CH-CH=CH-$, $-CH_2COCH_2-$, $-OCH_2O-$, $-OCH_2CH_2O-$, $-OCH_2CH_2CH_2O-$, $-OCH_2CH_2-$, $-CH_2CH_2NH-$, $-CH=CH-CH=N-$, $-COCH_2CO-$, $-SCH_2CH_2-$, $-SCH_2S-$, $-SCH_2CH_2S-$, $-C(CH_3)_2-CO-C(CH_3)_2-$, $-OCF_2O-$, $-OCF_2CHFO-$, $-OCF_2CHFO-$, $-OCF_2CF_2O-$, and $-OCF_2CFClO-$.

$R^6$ and $R^7$, or $R^7$ and $R^8$ representing a 5- or 6-membered saturated or unsaturated ring is preferably a saturated carbocyclic ring or a saturated ring containing an oxygen or a sulphur atom in the 4-position in the pyridine ring, e.g. $-CH_2CH_2CH_2-$, $-CH_2CH_2CH_2CH_2-$, $-O-CH_2CH_2-$, $-O-CN_2CH_2CH_2-$, $-SCH_2CH_2-$, or $SCH_2CH_2CH_2-$.

$R^1$, $R^2$, $R^3$ and $R^4$ when representing haloalkoxy is preferably a lower haloalkoxy. Especially preferred are lower fluoroalkoxy, or fluorochloroalkoxy groups, e.g. $OCF_3$, $OCHF_2$, $OCF_2CHF_2$, $OCF_2CF_3$, $OCF_2CF_3$, $OCF_2Cl$, $OCH_2CF_3$.

$R^7$ when representing alkoxy is exemplified by $OCH_2CF_3$, $OCH_2CF_2CF_3$ and $OCH_2CF_2CHF_2$.

$R^1$, $R^2$, $R^3$ and $R^4$ representing hydroxyalkyl is exemplified by $CH_2OH$, $CH_2CH_2OH$, $CH_2CH_2CH_2OH$, and $(CH_2)_4OH$.

$R^7$ when representing a dialkylamino group is preferably $-N(CH_3)_2$, or $-N(C_2H_5)_2$.

Examples of pyridine radicals are those which are 3,5-dimethyl-4-methoxy-, 3-methyl-4-methoxy, 5-ethyl-4-methoxy-, 4-methoxy-, 4-ethoxy-, 4-isopropoxy-, 3,5-dimethyl-, 3,4-dimethoxy-, 4,5-dimethoxy-, 3-methyl-4-

(2,2,2-trifluoro)ethoxy-, 3,4-dimethoxy-, 4,5-dimethoxy-, 3-methyl-4-ethylthio-, 3-methyl-4,5-dimethoxy-, 3,4,5-trimethyl-, 3-ethyl-4-methoxy-, 3-n-propyl-4-methoxy-, 3-isopropyl-4-methoxy-, 3-t-butyl-4-methoxy-substituted. Of special interest is the compound 2-[[(4-methoxy-3,5-dimethyl-2-pyridinyl)-methyl]-sulfinyl]-5-methoxy-1H-benzimidazole (omeprazole).

For the compounds with the general formula I containing an asymmetric centre, both the pure enantiomers and the racemic mixtures are within the scope of the present invention.

Accordingly, the invention relates to a method for the treatment of the ailment above by administering to a host in need thereof of a therapeutically effective amount of a compound of the formula I a pharmaceutical preparation for use in the treatment of the ailment above comprising a compound of the formula I as active ingredient.

a compound of the formula I for use in the manufacture of a medicament for the treatment of the ailment above

PHARMACOLOGICAL TEST

In order to evaluate the intraocular pressure lowering effect the following method was used.

A stock solution of 100 mM of the test compound was made up in a mixture of 4.5 ml of DMSO and 0.5 ml of 0.1 M phosphate buffer at pH 7.3. One hundred μl of the test compound stock solution was added to 1.9 ml of balanced salt solution to make a final concentration of 5 mM. This 5 mM solution of the test compound was used in the experimental eye. The control solution was composed of 100 μl of the DMSO-phosphate buffer solution added to balanced salt solution.

Twenty pigmented rabbits weighing 2 kg were used as the experimental animals. Pre-experiment eye examinations were performed on the rabbits and intraocular pressures were measured using a pneumotonometer (Digilab model 30R). The pneumotonometer was calibrated prior to each series of measurements. Proparacaine hydrochloride ½% was used as a local anaesthetic prior to each intraocular pressure measurement. Pre-treatment intraocular pressure measurements were done, then 50 μl of the experimental solution was placed on the right eye and 50 μl of the control solution was placed on the left eye of each rabbit.

Post-treatment intraocular pressures were performed on both eyes of each rabbit every 15 minutes for the first two hours, then every two hours for the next four hours, and a final intraocular pressure measurement was performed 24 hours following treatment.

The intraocular pressures of the experimental right eye were compared to the control fellow eye of each rabbit. Also comparisons were made between pre- and post-treatment intraocular pressures of each eye.

RESULTS

The compound 2-[[(4-methoxy-3,5-dimethyl-2-pyridinyl)-methyl]-sulfinyl]-5-methoxy-1H-benzimidazole was tested.

No evidence of ocular irritation was found in either experimental or control eyes of all 20 rabbits. The intraocular pressures in both experimental and control eyes decreased following treatment. Table 1 shows that this decrease in intraocular pressure was maximal at 2-4 hours following drug application and that the intraocular pressures returned to pre-treatment levels by 24 hours. There appeared to be a slightly greater decrease in intraocular pressure in the control eye when compared to the experimental eye, but this difference is not statistically significant. The maximum decrease in intraocular pressure was approximately 4 mm Hg or about 14% of the pre-treatment intraocular pressure.

TABLE 1

Effect of topical administration on the intraocular pressure in the rabbit.

| Time after administration [hr] | Pressure, mm Hg | |
| --- | --- | --- |
| | Left eye | Right eye |
| 0 | 27.7 | 28.1 |
| 0.28 | 27.1 | 27.1 |
| 0.51 | 26.6 | 27.0 |
| 0.74 | 26.4 | 26.4 |
| 1.02 | 26.3 | 26.3 |
| 1.30 | 25.4 | 26.0 |
| 1.48 | 25.3 | 26.3 |
| 1.76 | 25.1 | 25.7 |
| 2.04 | 24.6 | 25.1 |
| 3.98 | 24.1 | 25.9 |
| 6.02 | 25.2 | 26.4 |
| 24.00 | 28.0 | 28.8 |

ADMINISTRATION

For clinical use the compounds can be administered suitably either topically to the eye or by microinjection into the trabecular meshwork. For topical administration, the compound can be administered in solution or by another suitable vehicle such as oinment, together with a pharmaceutically acceptable carrier substance, e.g., physiological saline or ointment base. For compounds having limited water solubility the liquid carrier medium can contain an organic solvent, e.g., 3% methyl cellulose. Methyl cellulose provides, by its high viscosity, increased contact time between the compound and the eye surface, and therefore increased corneal penetration. Corneal penetration can also be increased by administering the compound mixed with an agent which slightly disrupts the corneal membrane, e.g., 0.025% benzalkonium chloride.

Administration can made by periodically (e.g., one time per week to ten times per day). When using a solution of the active substance, drops of the compound in solution can be administered using an eye dropper, such that an effective amount of the compound is delivered through the cornea to the trabecular meshwork. The amount of the compound to be delivered in one administration will depend on individual patient characteristics, e.g., severity of disease. A typical administration may be 1-100 drops to each eye per day and each drop may contain 25-100 microliters of a 1-25 mM solution of the compound, so that 0.0025 to 25 mmoles of the compound are delivered to each eye per day.

Direct microinjection of the solubilized compound into the trabecular meshwork offers the advantage of concentrating the compound in the location where it is needed, while avoiding the possibility of side effects resulting from generalized exposure of the eye to the compound. Microinjection also provides the advantages of permitting infrequent periodic administration, e.g., every few weeks, months, or even years, in contrast to the more frequent administrations required in the case of topical administration. Also, direct microinjection may promote the washing out of the trabecular meshwork of extracellular material interferring with fluid outflow. Dosage for microinjection, like that for topical administration, varies with the above-mentioned parameters. Typically, microinjection dosage is such that a final concentration of the compound within the trabecular meshwork of 0.001–0.1 mM is reached.

The compounds of the formula I can also be administered orally, rectally, parenterally or by other modes of administration, suitably in combination with a pharmaceutically acceptable carrier. The effect of the compounds of the formula I in the eye can be achieved by direct application or by using the systemic effect of the compounds.

What we claim is:

1. A method of decreasing elevated intraocular pressure in the eye of a human patient comprising administering to said eye a therapeutically effective amount of a compound of the formula I below, optionally together with a pharmaceutically acceptable carrier:

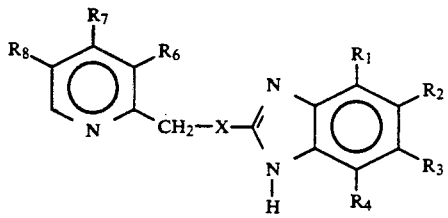

wherein

X is —S— or —SO—;

$R^1$, $R^2$, $R^3$ and $R^4$, which are the same or different, are (a) H
(b) alkyl of 1–8 carbon atoms
(c) alkoxy of 1–8 carbon atoms
(d) alkoxyalkyl of 1–3 carbon atoms in each alkyl
(e) alkoxyalkoxy of 1–3 carbon atoms in each alkyl
(f) halogen
(g) —CN
(h) —CF$_3$
(i) —NO$_2$
(j) —COR$^{10}$
(k) alkylthio of 1–6 carbon atoms in the alkyl part
(l) alkylsulfinyl of 1–7 carbon atoms in the alkyl part
(m) aryl-thio, -sulfinyl, -sulfonyl, -sulfonyloxy, oxysulfonyl, -sulfonamido or -aminosulfonyl, whereby each aryl group optionally is substituted by 1–3 substituents, the same or different and selected from halogen, CF$_3$ and (1–5C)alkoxy
(n) arylalkyl or arylalkoxy, of 1–6 carbon atoms in the alkyl and alkoxy parts, respectively, whereby the aryl part optionally is substituted by 1–3 substituents, the same or different and selected from halogen, CF$_3$, (1–5C) alkyl and (1–5C)alkoxy
(o) aryl or aryloxy, whereby each aryl group optionally is substituted by 1–3 substituents, the same or different and selected from the group consisting of halogen, CF$_3$, (1–5C)alkyl and (1–5C)alkoxy (p) haloalkoxy of 1–6 carbon atoms and 1–11 halogen atoms,
(q) hydroxyalkyl of 1–6 carbon atoms $R^6$ is
(a) H
(b) alkyl of 1–8 carbon atoms
(c) alkoxy of 1–8 carbon atoms
(d) halogen $R^8$ is
(a) H
(b) alkyl of 1–8 carbon atoms
(c) alkoxy of 1–6 carbon atoms
(d) halogen
(e) arylalkyl of 1–4 carbon atoms in the alkyl part $R^7$ is
(a) H
(b) alkyl of 1–7 carbon atoms
(c) alkoxy of 1–7 carbon atoms
(d) alkoxyalkyl of 1–3 carbon atoms in each alkyl part (e) alkoxyalkoxy of 1–3 carbon atoms in each alkyl part
(f) aryloxy, whereby the aryl group optionally is substituted by 1 and 2 substituents, the same or different and selected from the group consisting of halogen, CF$_3$, (1–3C)alkyl or (1–3C)alkoxy
(g) arylalkyl or arylalkoxy of 1–7 carbon atoms in the alkyl or alkoxy part, whereby the aryl part optionally is substituted by 1 or 2 substituents, the same or different and selected from the group consisting of halogen, CF$_3$, (1–3C)alkyl and (1–3C)alkoxy
(h) alkenyloxy of 1–7 carbon atoms in the alkenyl part
(i) alkynyloxy of 1–7 carbon atoms in the alkenyl part
(j) alkylthio of 1–7, carbon atoms in the alkyl part
(k) arylthio or arylalkylthio of 1–3, carbon atom in the alkyl part
(l) dialkylamino of 1–7, carbon atoms in the alkyl parts
(m) fluoroalkoxy of 2–5 carbon atoms and 1–9 fluorine atoms $R^{10}$ is
(a) alkyl of 1–6 carbon atoms
(b) alkoxy of 1–6 carbon atoms
(c) aryl;

as well as pharmaceutically acceptable salts thereof,

2. A method according to claim 1, wherein X is —S—.

3. A method according to claim 1, wherein X is —SO—.

4. A method according to claim 1 comprising administering 2-[[(4-methoxy-3,5-dimethyl-2-pyridinyl)-methyl]-sulfinyl]-5-methoxy-1H-benzimidazole.

5. A method of decreasing the intraocular pressure in the eye of a human patient comprising administering by microinjection to said eye of a therapuetically effective amount of a compound of the formula I as defined in claim 1, optionally together with a pharmaceutically acceptable carrier.

* * * * *